United States Patent
Koga

(12) 
(10) Patent No.: US 7,674,613 B2
(45) Date of Patent: Mar. 9, 2010

(54) LIVE BACTERIUM PREPARATION CONTAINING LACTIC ACID BACTERIUM AS ACTIVE INGREDIENT AND FOOD CONTAINING LACTIC ACID BACTERIUM

(75) Inventor: Yasuhiro Koga, Isehara (JP)

(73) Assignee: Frente International Co., Ltd. (JP)

( * ) Notice: Subject to any disclaimer, the term of this patent is extended or adjusted under 35 U.S.C. 154(b) by 885 days.

(21) Appl. No.: 10/508,340

(22) PCT Filed: Mar. 29, 2002

(86) PCT No.: PCT/JP02/03177

§ 371 (c)(1),
(2), (4) Date: May 3, 2005

(87) PCT Pub. No.: WO03/082027

PCT Pub. Date: Oct. 9, 2003

(65) Prior Publication Data

US 2007/0071737 A1    Mar. 29, 2007

(51) Int. Cl.
*C12N 1/20* (2006.01)
*C12N 1/12* (2006.01)
*C12N 1/00* (2006.01)
*A01N 63/00* (2006.01)

(52) U.S. Cl. .................. 435/252.9; 435/252.1; 435/243; 424/93.45; 424/93.1

(58) Field of Classification Search .............. 435/252.9, 435/252.1, 243; 424/93.45, 93.1
See application file for complete search history.

(56) References Cited

U.S. PATENT DOCUMENTS 4,726,943 A * 2/1988 Klueppel et al. .............. 424/54
4,746,512 A * 5/1988 Kawai et al. ............. 424/203.1

FOREIGN PATENT DOCUMENTS

WO     WO/02/16554 A1 * 2/2002

OTHER PUBLICATIONS

Katoh et al. 2002. English translation (machine translation) of WO/2002/16554 A1. p. 1-19.*

* cited by examiner

*Primary Examiner*—Taeyoon Kim
(74) *Attorney, Agent, or Firm*—Bacon & Thomas, PLLC

(57) ABSTRACT

Disclosed is a live bacterium preparation or food containing a lactic acid bacterium comprising a lactic acid bacterium, *Lactobacillus salivarius*, as an active ingredient. There is provided a live bacterium preparation and food containing a lactic acid bacterium that can prevent onset, recurrence and exacerbation of periodontal disease and/or dental caries caused by periodontopathic bacteria and cariogenic bacteria and can prevent generation of halitosis and maintain pH of saliva at a physiologically normal level by normalizing intraoral microflora.

15 Claims, 11 Drawing Sheets

LIVE BACTERIUM PREPARATION CONTAINING LACTIC ACID BACTERIUM AS ACTIVE INGREDIENT AND FOOD CONTAINING LACTIC ACID BACTERIUM

CROSS-REFERENCE TO RELATED APPLICATION

This application is a National Phase Application (35 USC 371) of PCT/JP02/03177.

TECHNICAL FIELD

The present invention relates to a drug (live bacterium preparation) for total oral care containing a lactic acid bacterium as an active ingredient for prevention and treatment of gingivitis, periodontitis, periodontal disease, caries and halitosis, food containing lactic acid bacterium and use thereof.

BACKGROUND ART

According to survey of the Japanese Ministry of Health, Labor and Welfare, it has been reported that the number of patients suffering from periodontal disease accounted for 18.2% of the national population according to the survey in 1975, but increased to 68.1% in 1993 and 72.9% in 1999, thereafter the number has increased steadily, and the presumed number of the patients has reached even 90 millions, and the current situation is that much expenditure is imposed on the dental region also from the viewpoint of medical economy.

For that reason, the authority has already decided to address prevention of periodontal disease in a nationwide scale in 1988, and has been working on development and promotion of the so-called "8020 movement".

However, currently, the number of patients has not decreased yet, and development of breakthrough methods for prevention and treatment of the disease are desired.

In recent years, it is pointed out that periodontal disease is not merely a disease as chronic infectious disease of the gingival tissues, but has a risk of causing circulatory system diseases such as cardiac infarct and destruction of blood vessel due to aneurysm, and periodontal disease also attract attentions as a risky factor for induction of diabetes mellitus and premature delivery. For treatment of periodontal disease, there has been no appropriate therapy so far, and treatment by dental techniques, that is, administration of germicides to a pathological site, surgical operation, oral administration of antibiotics and so forth, are practically used. However, long term consecutive administration of germicides or antibiotics for therapeutic treatment generates novel resistant bacteria due to the use thereof, and at the same time, it has many serious problems such as development of side effects due to the drug. Thus, it is the present situation that any satisfactory treatment method has not been necessarily established.

Therefore, for the purpose of prevention and treatment of periodontal disease or caries, the possibility of prevention or treatment of the aforementioned diseases by use of lactic acid bacteria has been studied as a method alternative to the administration of germicides or antibiotics.

As methods for prevention and treatment of periodontal disease and caries using lactic acid bacteria, a method of using, as an active ingredient, cells and/or aqueous extract of *Enterococcus faecium*, *Streptococcus equinus*, *Lactobacillus fermentum* or *Lactobacillus salivarius* are disclosed in Japanese Patent Laid-open Publication (Kokai) No. 61-91126 and Japanese Patent Publication (Kokoku) No. 4-52249. Further, in International Patent Publication WO99/07826, factors for suppressing the inhibitory activity for glucosyl transferase expressed or produced by *Lactobacillus* spp. V20 and *Streptococcus oralis* and development of caries, and the aforementioned lactic acid bacteria inhibiting production of hydrogen peroxide are studied.

Meanwhile, 400 or more kinds of bacteria inhabit in the human oral cavity, and the number of bacteria reaches even 10 billions. Incidentally, a number of bacteria at a level of $10^8$ to $10^9$ CFU/ml is detected in saliva. Therefore, a complicated microflora is formed in the human oral cavity (oral microbial flora), and thus it is extremely problematic to discuss effectiveness of prevention and treatment of periodontal disease and caries in humans based on extrapolation of results obtained in a simple in vitro system. In addition, in order to discuss the effectiveness on the premise of administration to human, it is necessary to also consider viability of live bacteria in a live bacterium preparation or food containing a lactic acid bacterium, as well as flavor and physicochemical properties of such a live bacterium preparation or food containing a lactic acid bacterium. However, in the aforementioned literatures concerning utilization of lactic acid bacteria in prevention and treatment of periodontal disease and caries, data of elimination or suppression of pathogenic bacteria of periodontal disease or caries obtained in an in vivo system using human or model animal, or data concerning viability of live bacteria in a live bacterium preparation or food containing a lactic acid bacterium, flavor and physicochemical properties of such a live bacterium preparation or food containing lactic acid bacterium are not disclosed at all.

As a bacterial strain used in a live bacterium preparation or food containing a lactic acid bacterium serving as means for prevention and treatment of periodontal disease and caries, of which administration to human is intended, a lactic acid bacterium strain that can definitely eliminate or suppress pathogenic bacteria of periodontal disease and caries, which are intraoral pathogenic bacteria, in a test using human and model animals should be selected. Further, when the lactic acid bacterium strain is used in a live bacterium preparation or food containing the lactic acid bacterium, it is essential that the lactic acid bacterium should show high viability, and it is preferred that the preparation or food shows superior flavor and physicochemical properties.

DISCLOSURE OF THE INVENTION

In view of such a state of the art concerning utilization of lactic acid bacteria in prevention or treatment of periodontal disease and caries as described above, an object of the present invention is to provide a lactic acid bacterium strain that can prevent onset, recurrence and exacerbation of periodontal disease and/or dental caries, of which causative bacteria are periodontopathic bacteria and cariogenic bacteria. Another object of the present invention is to provide a live bacterium preparation and food containing a lactic acid bacterium containing such a lactic acid bacterium strain as described above.

It is most important to select, as the aforementioned strain, a strain of which effectiveness is clinically verified for properties that it can eliminate or suppress pathogenic bacteria of periodontal disease and caries, which are intraoral pathogenic bacteria, further normalize the intraoral microflora to prevent generation of halitosis, maintain pH of saliva at a physiologically normal level and so forth.

The inventor of the present invention screened various lactic acid bacteria belonging to the genus *Lactobacillus* from the aforementioned viewpoint, as a result, found that *Lacto-* bacillus salivarius had the aforementioned properties, and thus accomplished the present invention.

Therefore, the present invention provides a live bacterium preparation or food containing a lactic acid bacterium, which contains, as an active ingredient, a lactic acid bacterium, Lactobacillus salivarius. The live bacterium preparation or food containing a lactic acid bacterium of the present invention can be used for normalization of intraoral microflora, prevention of onset and treatment of gingivitis, periodontitis and periodontal disease, prevention of onset and treatment of caries, prevention of generation of halitosis and elimination of halitosis, and so forth.

The present invention further provides a Lactobacillus salivarius TI 2711 strain (FERM BP-7974), as a particularly preferred strain of Lactobacillus salivarius, as well as cells and dry cells thereof. The aforementioned live bacterium preparation and food containing a lactic acid bacterium of the present invention particularly preferably contain the Lactobacillus salivarius TI 2711 strain (FERM BP-7974) as Lactobacillus salivarius.

The present invention also provides use of the lactic acid bacterium, Lactobacillus salivarius TI 2711 strain (FERM BP-7974), for preparation of a live bacterium preparation or food containing a lactic acid bacterium of the Lactobacillus salivarius TI 2711 strain (FERM BP-7974), and a composition containing the lactic acid bacterium, Lactobacillus salivarius TI 2711 (FERM BP-7974) strain, and an active ingredient having a mechanism of action different from that of the strain.

BEST MODE FOR CARRYING OUT THE INVENTION

Figure 1:
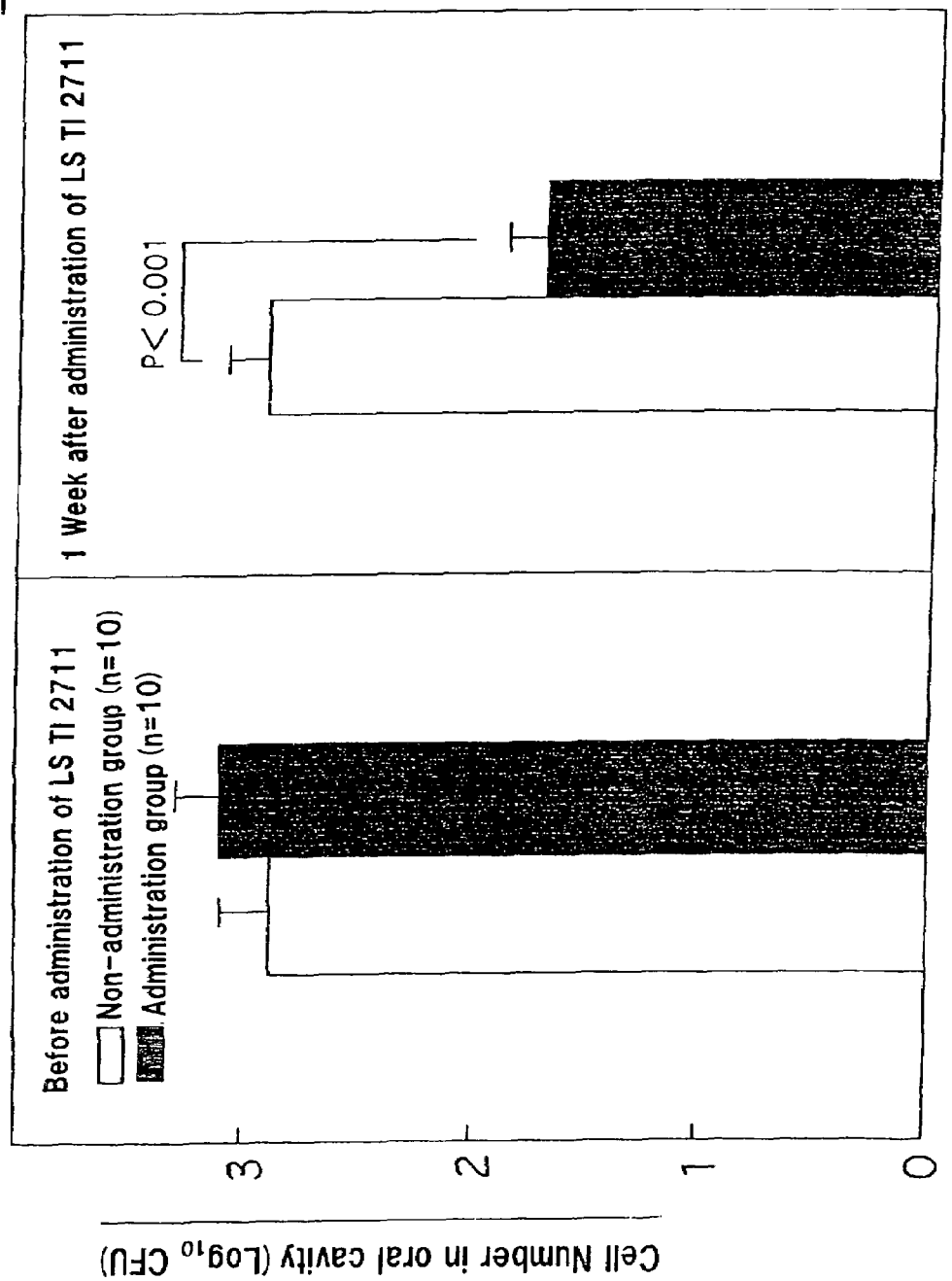
FIG. 1 is a graph showing suppression effect (in vivo) of L. salivarius TI 2711 strain on the mouse intraoral P. gingivalis JCM 8525 strain.

In order to select a lactic acid bacterium strain that met the aforementioned object of the present invention, the inventor of the present invention tested many stock strains (30 strains) of the genus Lactobacillus isolated from oral cavities of healthy subjects and selected an optimum strain according to the following procedures.

1. A strain that proliferated in the shortest time in comparison with normal Lactobacillus rods was selected (see Test Example 1, (1)).

2. Mixed culture of each of the stock strains (30 strains) of the genus Lactobacillus and each of clinically isolated strains of major periodontopathic bacteria, Porphyromonas gingivalis, Prevotella intermedia and Prevotella nigrescens, was performed, and a strain that could powerfully suppress growth of periodontopathic bacteria was selected (for example, see Test Example 1, (2) using Porphyromonas gingivalis).

3. Then, mixed culture of each of the stock strains (30 strains) of genus Lactobacillus of the above section 1 and each of Streptococcus mutans and Streptococcus sobrinus, which are clinically isolated strains of major causative bacteria of caries, was performed, and a strain that could significantly suppress growth of cariogenic bacteria was selected (for example, see Test Example 1, (3) using Streptococcus mutans).

4. Further, in order to verify the effectiveness on caries, insoluble glucan (major causative substance of caries) in the mixed culture was quantified, and a strain that significantly suppressed production of insoluble glucan was selected (see Test Example 1, (3)).

5. Then, in order to verify the effectiveness of the Lactobacillus salivarius TI 2711 strain selected by the in vitro tests of the aforementioned sections 1 to 4, an infection model test using germfree mice was performed (see Test Example 2). The outline is as follows.

1) A periodontopathic bacterium, Porphyromonas gingivalis, was inoculated into the oral cavity of germfree mouse and colonized therein. Then, the Lactobacillus salivarius TI 2711 strain was orally administered, and the number of Porphyromonas gingivalis cells was counted to verify significant suppression of the growth (see Experiment 1).

2) A cariogenic bacterium, Streptococcus mutans, was inoculated into the oral cavity of germfree mouse and colonized therein. Then, the Lactobacillus salivarius TI 2711 strain was orally administered, and the number of Streptococcus mutans cells was counted to verify significant suppression of the growth (see Experiment 2).

6. As a clinical test, healthy volunteers (n=57) were raised with their informed consent, and intraoral saliva was collected from them. The number of total bacteria was counted, and the numbers of periodontopathic bacteria (colonies of Gram-negative BPAR (black-pigmented anaerobic rods)), cariogenic bacteria, Streptococcus mutans, and useful bacteria, Lactobacillus rods were counted, respectively. Furthermore, pH of the saliva and the amount of insoluble glucan in the saliva were counted, and halitosis in the oral cavity was measured by using Halimeter.

Thereafter, tablets (confectionary tablets) of Lactobacillus salivarius TI 2711 were taken by the volunteers for an intake term of 8 weeks. After the intake of 4 weeks and after the intake of 8 weeks, i.e., at the end of the intake, all of the aforementioned items were measured, and effectiveness or side effects after the intake were examined by inquiry. The results of all of the items were statistically processed (Wilcoxon method). As a result, significant differences were objectively observed between the values before and after the intake for all of the items. Furthermore, overall evaluation was performed based on the results together with the results of the inquiry, and the effectiveness was also clearly verified also in a clinical test (see Test Example 3).

The bacteriological characteristics of the Lactobacillus salivarius TI 2711 strain selected in the aforementioned sections 1 to 4 as a strain meeting the object of the present invention are as follows.

A: Morphological Characteristics
   Cell morphology: rod-shaped bacterium
   Cell size: 0.6 to 0.9×1.7 to 5.2 μm
   Mobility: none
   Sporogenesis: none
   Gram-staining: positive B: Physiological Characteristics (Positive: +, Negative: −)
   Gas production: −
   Catalase: −
   Gelatin liquefying ability: −
   Behavior to oxygen: facultative aerobic
   Indole production: −
   Nitrate reducing ability: −
   Hydrogen sulfide production: −
   Optically active isomer of produced lactic acid: L-isomer C: Assimilation of Sugars (Assimilation Positive: +, Assimilation Negative: −)
   Arabinose: −
   Amygdalin: −
   Cellobiose: −
   Esculin: −
   Galactose: +
   Glucose: +
   Fructose: +
   Gluconic acid: −
   Lactose: +
   Maltose: +
   Mannitol: +
   Mannose: +
   Melibiose: +
   Raffinose: +
   Melezitose: −
   Rhamnose: +
   Ribose: −
   Sorbitol: +
   Sucrose: +
   Xylose: −
   Salicin: −
   Trehalose: +

Based on the foregoing bacteriological characteristics, and according to the classification standards of Bergey's Manual of Systematics Bacteriology, vol. 2, (1986) and Tomotari Mitsuoka, Chonaikin no Sekai (World of Enterobacteriaceae), Soubunsha, 1980), the strain of the present invention selected in the aforementioned sections 1 to 4 was identified as *Lactobacillus salivarius*, and the strain was designated as *Lactobacillus salivarius* TI 2711 strain. The strain was deposited at the independent administrative corporation, National Institute of Advanced Industrial Science and Technology, International Patent Organism Depositary (Tsukuba Central 6, 1-1, Higashi 1-Chome, Tsukuba-shi, Ibaraki-ken, Japan, postal code: 305-8566) on Mar. 26, 2002, and given with an accession number of FERM BP-7974.

The lactic acid bacterium strain of the present invention, *Lactobacillus salivarius* TI 2711 strain, can suppress or arrest adhesion of periodontopathic bacteria and cariogenic bacteria to gingival tissues, periodontal pockets and teeth and growth thereof and can suppress or eliminate pathogenic bacteria present in the oral cavity, when it is orally taken by a host such as human. Thus, there is provided an extremely effective means for prevention and treatment of periodontal disease and caries, which should be called national diseases. Such an interaction between a host and intraoral microbes is widely observed in the natural world, and this is understood as commensalism, parasitism or antagonism phenomenon among relationships between a host and microbes.

Hereafter, use of the lactic acid bacterium strain of the present invention (*Lactobacillus salivarius* TI 2711 strain) will be described.

The lactic acid bacterium strain of the present invention (*Lactobacillus salivarius* TI 2711 strain) can be administered as an active ingredient as it is or as a single active ingredient preparation together with a suitable additive, or may be administered simultaneously with or a mixture with another active ingredient, for example, other oral care drugs having an action mechanism different from that of the strain. Preferred examples of the dosage form include, for example, powders, granules, tablets, capsules, syrups and so forth, and the strain can be orally administered safely. When the lactic acid bacterium strain of the present invention is used in these dosage forms, it is preferable to formulate dry cells (live bacteria) of the lactic acid bacterium strain of the present invention into a preparation. The dry cells (live bacteria) of the lactic acid bacterium strain of the present invention can be obtained in a conventional manner, for example, by culturing the lactic acid bacterium strain of the present invention as pure culture, collecting cells by a method of, for example, centrifugation, adding a suitable stabilizer to the cells, and lyophilizing the cells.

The aforementioned various preparations can also be prepared in a conventional manner, and they can be prepared by using known pharmaceutical additives usually used in the field of pharmaceutical preparation such as excipients, binders, disintegrating agents, coating agents, lubricating agents, stabilizers, corrigents, solubilizing aids, lubricants, suspending agents and diluents together with the lactic acid bacterium strain of the present invention as the active ingredient.

The doses of the aforementioned various preparations may vary depending on type, severity etc. of objective disease, and for example, preparations can be administered in an amount of about 1 mg to 2,000 mg per day in terms of dry cells of the lactic acid bacterium strain of the present invention once or several times in a day depending on symptoms.

Alternatively, the lactic acid bacterium strain of the present invention may be used by adding it to a wide range of general foods including confectioneries such as confectionary tablets, chewing gums and candies, and pickles such as Korean pickles, and thus foods containing a lactic acid bacterium can be provided. Also when the lactic acid bacterium strain of the present invention is used in a food, it is preferable to use dry cells (live bacteria) of the lactic acid bacterium strain of the present invention, and it can be added to a wide range of general foods optionally together with additives acceptable in foods.

Further, the lactic acid bacterium strain of the present invention can be taken in the form of a fermented food such as yogurt. Such a fermented food can be prepared by, for example, inoculating the lactic acid bacterium strain of the present invention together with a dairy farming lactic acid bacterium such as *Lactobacillus bulgaricus, Lactobacillus acidophilus, Lactobacillus helveticus, Streptococcus thermophilus* and *Streptococcus lactis*, which are starter bacteria for yogurt production, to a fermentation raw material such as cow's milk and sheep's milk and performing mixed culture or performing single culture of each bacterium in the fermentation raw material and then mixing the cultures.

In order to find a substance showing additive or synergistic effect with the lactic acid bacterium strain of the present invention and thereby further enhance the effect of the lactic acid bacterium strain of the present invention, the inventor of the present invention investigated effect of compositions containing an oligosaccharide or sugar alcohol together with the lactic acid bacterium strain of the present invention using caries as an index. As a result, it was found that when a sugar alcohol, erythritol, is used with the lactic acid bacterium strain of the present invention, a synergistic effect was exhibited in suppression of production of insoluble glucan compared with the anti-caries effect of each substance alone (see Test Example 4).

It is generally known that sugar alcohols (xylitol, maltitol, sorbitol, erythritol etc.) and oligosaccharides (fructo-oligosaccharide, xylo-oligosaccharide, kestose, rhafinose etc.) are effective to caries. However, the synergistic effect or additive effect provided by these sugar alcohols and oligosaccharides and a lactic acid bacterium strain greatly differs depending on selection of the lactic acid bacterium strain.

These useful sugar alcohols and oligosaccharides can be used each alone or in a combination thereof in the live bacterium preparation or food containing a lactic acid bacterium of the present invention. These sugar alcohols and oligosaccharides can also function as an excipient or sweetener. Types and blending ratios of these sugar alcohols and oligosaccharides are not particularly limited, and an arbitrary sugar alcohol or oligosaccharide can be used at an arbitrary ratio. For example, in the case of a confectionary tablet, a product containing an arbitrary sugar alcohol or oligosaccharide at an arbitrary ratio can be easily prepared by appropriately selecting a tablet composition, conditions such as compression pressure and hardness of confectionary tablet and using a conventional tablet making technique.

The present invention will be explained in more detail with reference to the following examples and test examples. However, the present invention is not limited by these examples.

TEST EXAMPLE 1

Screening of Lactic Acid Bacterium Strain (Genus *Lactobacillus*) Suitable for Suppression of Intraoral Pathogenic Bacteria (1) Test for Examining Proliferation Property Each of the 30 strains of lactic acid bacteria belonging to genus *Lactobacillus* shown in Table 1 was inoculated into the MRS broth (Difico) in an amount of $1 \times 10^7$ CFU/ml and cultured at 37° C. for 6 hours under an aerobic condition, and then the number of viable bacteria was counted by the agar plate method.

That is, 1 ml of the culture broth of each strain after the culture for 6 hours was serially diluted with an anaero dilution buffer (4.5 g/l of $KH_2PO_4$, 6.0 g/l of $Na_2HPO_4$, 0.5 g/l of cysteine hydrochloride, 0.5 g/l of agar, 0.5 g/l of Tween 80), 0.1 ml of each dilution was inoculated onto the MRS agar medium (agar plate in which 1.5% agar was added to the MRS broth) and cultured at 37° C. for 48 hours under an anaerobic condition. Then, the number of colonies was counted and multiplied by the dilution times to obtain the number of viable bacteria. The results are shown in Table 1.

(2) Test of Activity for Suppressing Major Pathogenic Bacterium of Periodontopathic Bacterium, *Porphyromonas gingivalis* JCM 8525 Strain The *Porphyromonas gingivalis* JCM 8525 strain (cell number: $1 \times 10^6$ CFU/ml) alone (control) or a mixture thereof with each of the 30 strains of lactic acid bacteria shown in Table 1 (cell number: $1 \times 10^6$ CFU/ml) was inoculated into 10 ml of a liquid medium consisting of GAM bouillon (Nissui) containing 0.7% glucose. After the cells were cultured at 37° C. for 12 hours under an anaerobic culture condition, the number of cells of *Porphyromonas gingivalis* in each culture broth was counted by the agar plate method to obtain a ratio of the number of viable cells of *Porphyromonas gingivalis* obtained by the mixed culture with a bacterium of the genus *Lactobacillus* relative to the number of viable cells of *Porphyromonas gingivalis* obtained by culturing *Porphyromonas gingivalis* alone (control, 100%).

For counting the cell number of *Porphyromonas gingivalis* by the agar plate method, only *Porphyromonas gingivalis* was grown by using the EG-CM medium consisting of EG agar medium (Nissui) containing 10 µg/ml of gentamycin as a selection medium, and then the number of the bacteria was counted. That is, 1 ml each of the culture broth in which *Porphyromonas gingivalis* alone had been cultured or the culture broth in which the mixed culture with each of the lactic acid bacteria strains (30 strains) had been performed was taken and serially diluted with the aforementioned anaero dilution buffer, and 0.1 ml of each dilution was spread on the aforementioned EG-GM agar plate by using a Conradi's bar and anaerobically cultured at 37° C. for 48 to 72 hours. Then, the number of the obtained colonies was counted and multiplied with the dilution times to obtain the number of viable bacteria.

The ratio of the number of viable bacteria of *Porphyromonas gingivalis* obtained by the mixed culture with a bacterium of genus *Lactobacillus* relative to the number of viable bacteria of *Porphyromonas gingivalis* obtained by culture of *Porphyromonas gingivalis* alone (control, 100%) was considered as a survival rate of *Porphyromonas gingivalis*, and the survival rate was calculated in accordance with the following equation. The results are shown in Table 1 as the survival rate of *P. gingivalis* (%) Accordingly, an inhibition ratio (%) of a bacterium of the genus *Lactobacillus* for *P. gingivalis* is expressed by a value (%) obtained by subtracting the survival rate of *P. gingivalis* (%) from that of the control (100%).

Survival rate=(Cell number of *P. gingivalis* in mixed culture broth)/(Cell number of *P. gingivalis* cultured alone)×100

(3) Test of Suppression of Major Pathogenic Bacterium of Caries, *Streptococcus mutans* MT 8148 Strain, and Suppression of Insoluble Glucan Production In a volume of 5 ml of a liquid medium consisting of GAM bouillon (Nissui) containing 0.7% glucose and 3% sucrose was placed into a centrifugal sample collection tube and inoculated with *Streptococcus mutans* MT 8148 strain (cell number: $1 \times 10^6$ CFU/ml) alone (control) or a mixture thereof with each of the 30 strains of the lactic acid bacteria (cell number: $1 \times 10^6$ CFU/ml) shown in Table 1. After the cells were cultured at 37° C. for 24 hours under an aerobic condition, the number of viable cells of *Streptococcus mutans* in each culture broth was counted by the agar plate method to obtain a ratio of the number of viable bacteria of *Streptococcus mutans* obtained by the mixed culture with a bacterium of the genus *Lactobacillus* relative to the number of viable bacteria of *Streptococcus mutans* obtained by culture of *Streptococcus mutans* alone (control, 100%).

For counting the cell number of *Streptococcus mutans* by the agar plate method, only *Streptococcus mutans* was grown by using the TCYSB agar medium (40 g/l of tripticase soy agar (BBL), 0.3 g/l of cystine, 5 g/l of yeast extract, 200 g/l of sucrose, 5 g/l of agar, 10 U/ml of bacitracin) as a selection medium, and then the cell number was counted. That is, 1 ml of each of the aforementioned culture broths was taken and serially diluted with the aforementioned anaero dilution buffer, and 0.1 ml of each dilution was spread on the aforementioned selection medium plate and incubated at 37° C. for 72 hours. The colonies produced on the plate were counted and multiplied by the dilution times to obtain the number of viable cells.

The ratio of the number of viable bacteria of *Streptococcus mutans* obtained by the mixed culture with a bacterium of genus *Lactobacillus* relative to the number of viable bacteria of *Streptococcus mutans* obtained by culture of *Streptococcus mutans* alone (control, 100%) was considered as a survival rate of *Streptococcus mutans*, and the survival rate was calculated in the same manner as (2) mentioned above. The results are shown in Table 1 as the survival rate of *Strepto-* bition ratio (%) of a bacterium of the genus *Lactobacillus* for insoluble glucan production by *S. mutans* is represented by a value (%) obtained by subtracting a production rate (%) of insoluble glucan produced by *S. mutans* from the control (100%).

TABLE 1

Proliferation property, suppression effect (in vitro) on *P. gingivalis* JCM 8525 strain and *S. mutans* MT 8148 strain and effect for suppressing insoluble glucan production of various lactic acid bacteria strains of genus *Lactobacillus*

| | Genus *Lactobacillus* | | Culture condition | | | |
|---|---|---|---|---|---|---|
| | | | Aerobic Proliferation property (cell number after 6 hours/ml) | Anaerobic Survival rate of *P. gingivalis* (%) | Aerobic Survival rate of *S. mutans* (%) | Aerobic Production ratio of insoluble glucan (%) |
| (1) | *Lactobacillus acidophilus* | A | $5.0 \times 10^7$ | 101 | 72 | 60 |
| (2) | *L. acidophilus* | B | $3.0 \times 10^7$ | 111 | 111 | 80 |
| (3) | *L. casei* | TI1001 | $2.0 \times 10^7$ | 106 | 106 | 100 |
| (4) | *L. casei* | TI1002 | $6.2 \times 10^7$ | 100 | 100 | 98 |
| (5) | *L. rhamnosus* | TI1003 | $7.2 \times 10^7$ | 111 | 111 | 69 |
| (6) | *L. gasseri* | TI1004 | $8.2 \times 10^8$ | 55 | 55 | 11 |
| (7) | *L. gasseri* | TI1005 | $4.6 \times 10^8$ | 60 | 60 | 8 |
| (8) | *L. gasseri* | TI1006 | $6.0 \times 10^8$ | 65 | 65 | 15 |
| (9) | *L. johnsonii* | TI1008 | $4.0 \times 10^8$ | 82 | 4 | 70 |
| (10) | *L. salivarius* | ATCC11741 | $1.8 \times 10^9$ | 5.2 | 0.9 | 28 |
| (11) | *L. salivarius* | ATCC11742 | $1.2 \times 10^9$ | 10 | 1.2 | 30 |
| (12) | *L. salivarius* | TI1101 | $2.0 \times 10^9$ | 5 | 0.5 | 26 |
| (13) | *L. salivarius* | TI1102 | $3.0 \times 10^9$ | 1.0 | 0.1 | 31 |
| (14) | *L. salivarius* | TI1103 | $2.2 \times 10^9$ | 5.2 | 2.0 | 28 |
| (15) | *L. salivarius* | TI1104 | $1.6 \times 10^9$ | 10.2 | 1.8 | 28 |
| (16) | *L. salivarius* | TI1109 | $1.8 \times 10^9$ | 5.0 | 3.0 | 26 |
| (17) | *L. salivarius* | TI2700 | $2.6 \times 10^9$ | 0.5 | 4.0 | 28 |
| (18) | *L. salivarius* | TI2703 | $2.0 \times 10^9$ | 4.8 | 2.6 | 26 |
| (19) | *L. salivarius* | TI2704 | $2.0 \times 10^9$ | 5.6 | 3.2 | 32 |
| (20) | *L. salivarius* | TI2705 | $3.0 \times 10^9$ | 0.1 | 1.0 | 28 |
| (21) | *L. salivarius* | TI2706 | $3.2 \times 10^9$ | 0.1 | 0.8 | 22 |
| (22) | *L. salivarius* | TI2707 | $2.4 \times 10^9$ | 0.2 | 2.8 | 30 |
| (23) | *L. salivarius* | TI2708 | $2.2 \times 10^9$ | 0.5 | 2.2 | 30 |
| (24) | *L. salivarius* | TI2709 | $3.0 \times 10^9$ | 0.05 | 1.0 | 28 |
| (25) | *L. salivarius* | TI2710 | $3.6 \times 10^9$ | 0.05 | 0.5 | 25 |
| (26) | *L. salivarius* | TI2711 | $4.0 \times 10^9$ | 0.002 | 0.05 | 20 |
| (27) | *L. salivarius* | TI2714 | $2.2 \times 10^9$ | 0.005 | 0.1 | 21 |
| (28) | *L. salivarius* | TI2715 | $2.1 \times 10^9$ | 10.1 | 0.1 | 26 |
| (29) | *L. salivarius* | T12721 | $3.0 \times 10^9$ | 1.0 | 0.08 | 22 |
| (30) | *L. salivarius* | TI2722 | $3.2 \times 10^9$ | 2.0 | 0.08 | 24 |
| (31) | Control * | | | 100 | 100 | 100 |

* Control is each of the cell numbers obtained by culturing *P. gingivalis* and *S. mutans* alone, which were taken as 100(%).

*coccus mutans* (%). Accordingly, an inhibition ratio (%) of a bacterium of the genus *Lactobacillus* for *S. mutans* is expressed by a value (%) obtained by subtracting the survival rate of *S. mutans* (%) from that of the control (100%).

Further, for the measurement of insoluble glucan, insoluble glucan adhered to each sample collection tube containing the aforementioned culture broth was sufficiently scraped with a spatula, and the culture broth was centrifuged at 3,000 rpm for 15 minutes to collect the precipitates. The precipitates were washed with PBS (Phosphate Buffer Solution) twice and added with 5 ml of PBS to obtain a specimen for measurement. The insoluble glucan was quantified by the phenol/sulfuric acid method (Reiko Takahashi, Experimental Methods for Biochemistry, vol. 23, Supplement, Methods for Studying Sugars, Proteins and Sugar Chains). The results are shown in Table 1 as a ratio of an amount of insoluble glucan obtained by the mixed culture with each bacterium of the genus *Lactobacillus* relative to an amount of insoluble glucan obtained by the culture of *Streptococcus mutans* alone (production ratio of insoluble glucan (%)). Accordingly, an inhi- From the results shown in Table 1, it became clear that, among the 30 strains of genus *Lactobacillus*, the superior strain showing the best proliferation property, most strongly suppressing proliferation of the periodontopathic bacterium, *Porphyromonas gingivalis* and the cariogenic bacterium, *Streptococcus mutans*, and producing little insoluble glucan was the *Lactobacillus salivarius* TI 2711 strain of No. 26.

TEST EXAMPLE 2

In Vivo Effectiveness of *Lactobacillus salivarius* TI 2711 Strain on *Porphyromonas gingivalis* (Periodontopathic Bacterium) and *Streptococcus mutans* (Cariogenic Bacterium) in Germfree Mouse Oral Cavity (1) Test Methods Experiment 1

Four-week old germfree BALB/C mice were divided into a control group (post-infection non-administration group, n=10) and a post-periodopathic bacterium infection administration group (n=10). $1 \times 10^9$ CFU/0.5 ml of the periodontopathic bacterium, *Porphyromonas gingivalis* JCM 8525, was inoculated into oral cavities of mice of the post-infection administration group and the control group, respectively, for consecutive three days, three times in total. Then, one week after the establishment of the infection, the lactic acid bacterium strain of the present invention, *Lactobacillus salivarius* TI 2711 strain (cell number: $1 \times 10^9$ CFU/0.5 ml), was further administered similarly to the mice of the post-infection administration group for consecutive three days, three times in total.

Thereafter, the interior of the oral cavity of each infected mouse was sufficiently wiped with an aseptic swab sufficiently impregnated with the anaero dilution buffer to collect the whole saliva in the oral cavity after 1, 2 and 4 weeks, respectively, and the cell number of *Porphyromonas gingivalis* contained in the saliva was counted. The cell number of *Porphyromonas gingivalis* was counted in the same manner as in Test Example 1, (2).

Experiment 2

Four-week old germfree BALB/C mice were divided into a control group (post-infection non-administration group, n=10) and a post-cariogenic bacterium infection administration group (n=10). $1 \times 10^9$ CFU/0.5 ml of the cariogenic bacterium, *Streptococcus mutans* MT 8148, was inoculated into oral cavities of mice of the post-infection administration group and the control group, respectively, for consecutive three days, three times in total. Then, one week after the establishment of the infection, the lactic acid bacterium strain of the present invention, *Lactobacillus salivarius* TI 2711 strain (cell number: $1 \times 10^9$ CFU/0.5 ml), was further administered similarly to the mice of the post-infection administration group for consecutive three days, three times in total.

Thereafter, the interior of the oral cavity of each infected mouse was sufficiently wiped with an aseptic swab sufficiently impregnated with the anaero dilution buffer to collect the whole saliva in the oral cavity after 1, 2 and 4 weeks, respectively, and the cell number of *Streptococcus mutans* MT8148 contained in the saliva was counted. The cell number of *Streptococcus mutans* was counted in the same manner as in Test Example 1, (3).

Figure 10:
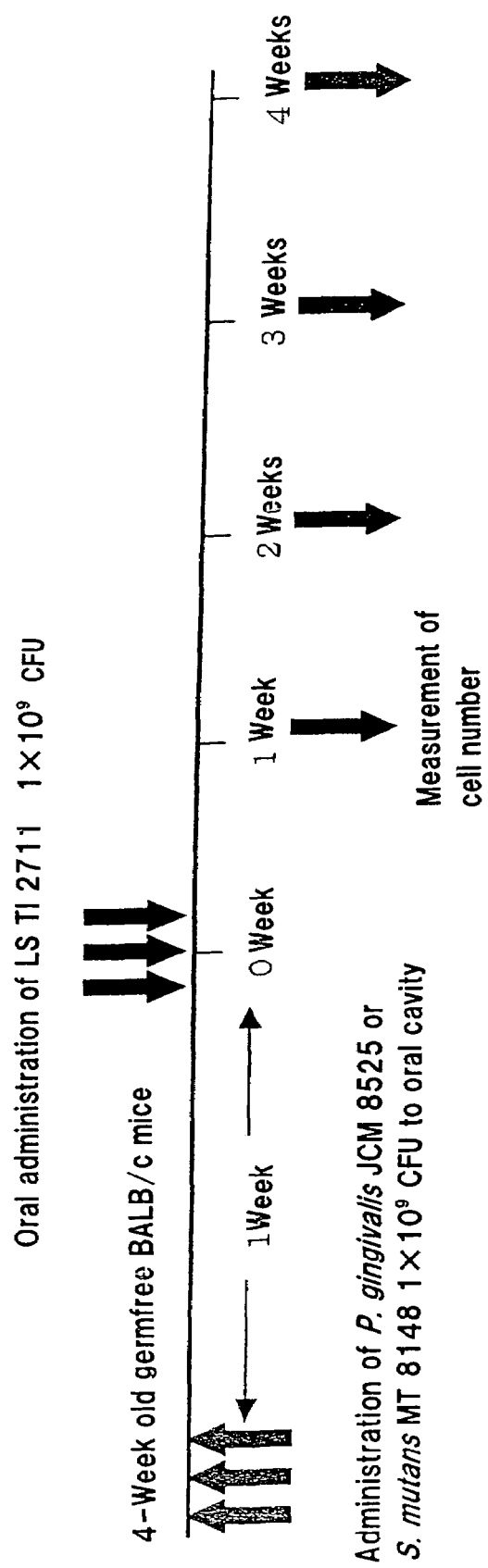
FIG. 10 is a diagram showing outlines of the protocols of Experiments 1 and 2 in Test Example 2.

Outlines of the in vivo protocols of Experiments 1 and 2 described above are shown in FIG. 10. In addition, the results of Experiments 1 and 2 are shown in FIG. 1 and FIG. 2.

(Test Results)

As clearly seen from the results of Experiment 1 shown in FIG. 1, in comparison of the cell numbers of the periodontopathic bacterium, *Porphyromonas gingivalis*, before and after the administration of the lactic acid bacterium strain of the present invention, *Lactobacillus salivarius* TI 2711 strain, to the germfree mice (BALB/b), the cell number of *Porphyromonas gingivalis* was clearly reduced after the administration with a significant difference of P<0.001 in a significant different test based on the Wilcoxon method.

Figure 2:
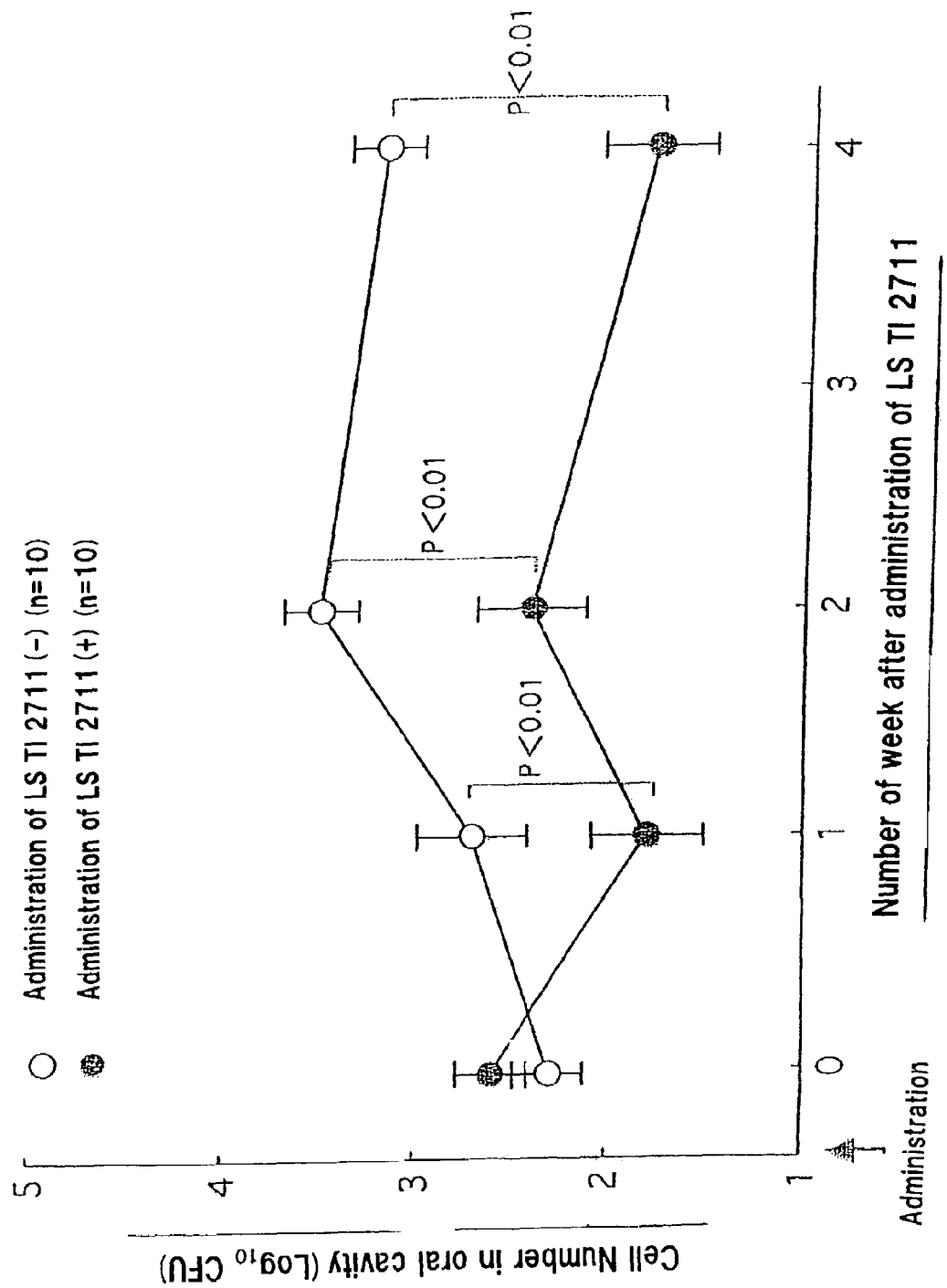
FIG. 2 is a graph showing suppression effect (in vivo) of L. salivarius TI 2711 strain on the mouse intraoral S. mutans MT 8148 strain.

As clearly seen from the results of Experiment 2 shown in FIG. 2, when the lactic acid bacterium strain of the present invention, *Lactobacillus salivarius* TI 2711 strain, was administered to the germfree mice (BALB/c) over 4 weeks, and variation of the cell number of the cariogenic bacterium, *Streptococcus mutans* MT 8148 strain, was investigated, it was demonstrated that the cell number was already significantly reduced after one week of the administration with P<0.01 compared with the number before the administration, and the decrease of the cell number continued even after fourth weeks with statistical significance (P<0.01).

TEST EXAMPLE 3

Protocol of Clinical Test

A clinical test was conducted according to the following protocol for 57 healthy volunteers with written informed consent.

Confectionary tablets containing 140 mg (cell number: $1 \times 10^8$ CFU/g) per tablet of lyophilized cell powder of the lactic acid bacterium strain of the present invention, *Lactobacillus salivarius* TI 2711 strain, were prepared and taken by each volunteer between meals in an amount of five tablets per time five times a day, i.e., 25 tablets in total per day. Each volunteer took the tablets every day over an intake term of 2 months, and collection of saliva, measurement of halitosis and doctor's inquiry were performed.

As the first inspection, collection of saliva, measurement of halitosis (Halimeter C21, manufactured by Interscan, USA) and inquiry were performed before the intake. The second inspection was similarly performed after the intake of four weeks, and the third final inspection was performed after the intake of eight weeks.

Figure 11:
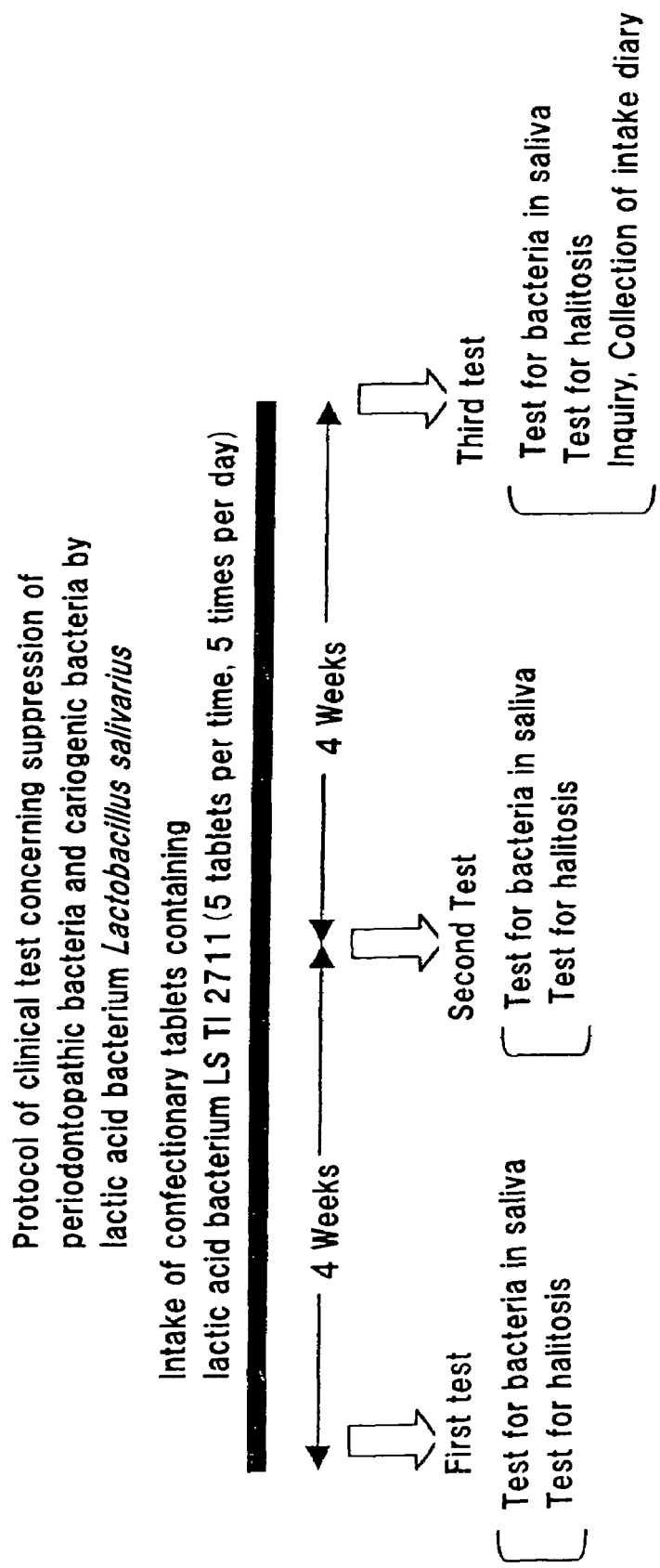
FIG. 11 is a diagram showing outline of the protocol of the clinical test in Test Example 3.

The protocol of the clinical test in this test example is outlined in FIG. 11.

(a) Method for Counting Cell Number in Saliva

In a volume of 100 µl of collected saliva of each of the healthy volunteers (n=57) was added to 900 µl of a sterilized anaero dilution buffer (see Test Example 1, (1)) to obtain a stock solution (×1-fold solution), and this solution was serially diluted to obtain ×3, ×5 and ×6-fold dilutions. In a volume of 0.1 ml of each dilution was quantified, and coated and spread on a preliminarily prepared agar plate medium of the selection medium shown below with a Conradi's bar. Thereafter, anaerobic culture was performed at 37° C. for 72 hours, and then the numbers of emerged colonies was counted to obtain number of the total bacteria, number of *Lactobacilli*, number of periodontopathic bacteria and number of cariogenic bacterium group bacteria. Then, one loop of each colony was taken and subjected to Gram-staining, and the result was confirmed under a microscope.

Selection Medium

Number of total bacteria: BL agar medium and EG agar medium *Lactobacilli*: Modified LBS agar medium Periodontopathic bacteria (BPAR=Gram-negative black-pigmented anaerobic rods): EG-GM agar medium, BL agar medium Caries bacterium group bacteria (*Streptococcus mutans, S. sobrinus*): TCYSB agar medium (b) Quantification of Insoluble Glucan: the Phenol/Sulfuric Acid Method was Used.

(c) Measurement of Halitosis: Halimeter C21 (Manufactured by Interscan, USA) was Used, and the Measurement Temperature was 20° C.

(d) Measurement of pH: Small-Size pH Meter (Manufactured by Horiba Seisakusho)

(Test Results)

(1) Total Number of Bacteria in Oral Cavity

Figure 3:
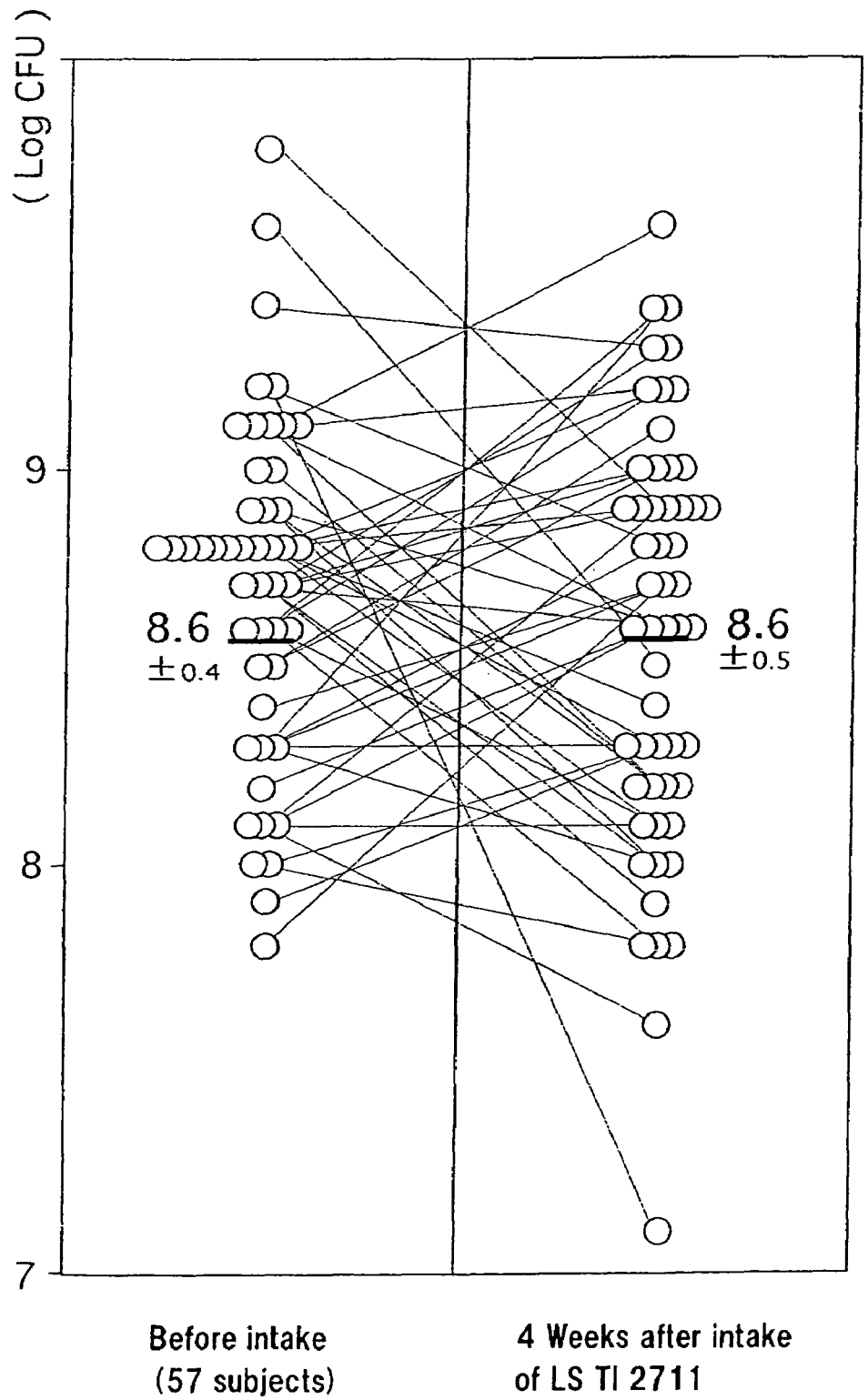
FIG. 3 is a graph showing change in the total number of human intraoral bacteria.

The obtained results for the total number of bacteria are shown in FIG. 3. As shown in FIG. 3, no significant difference was recognized between the total numbers of bacteria in a human oral cavity before the intake of confectionary tablets and after the intake of 4 weeks.

(2) Variation in Number of Intraoral Periodontopathic Bacteria (BPAR=Gram-Negative Black-Pigmented Anaerobic Rods)

Figure 4:
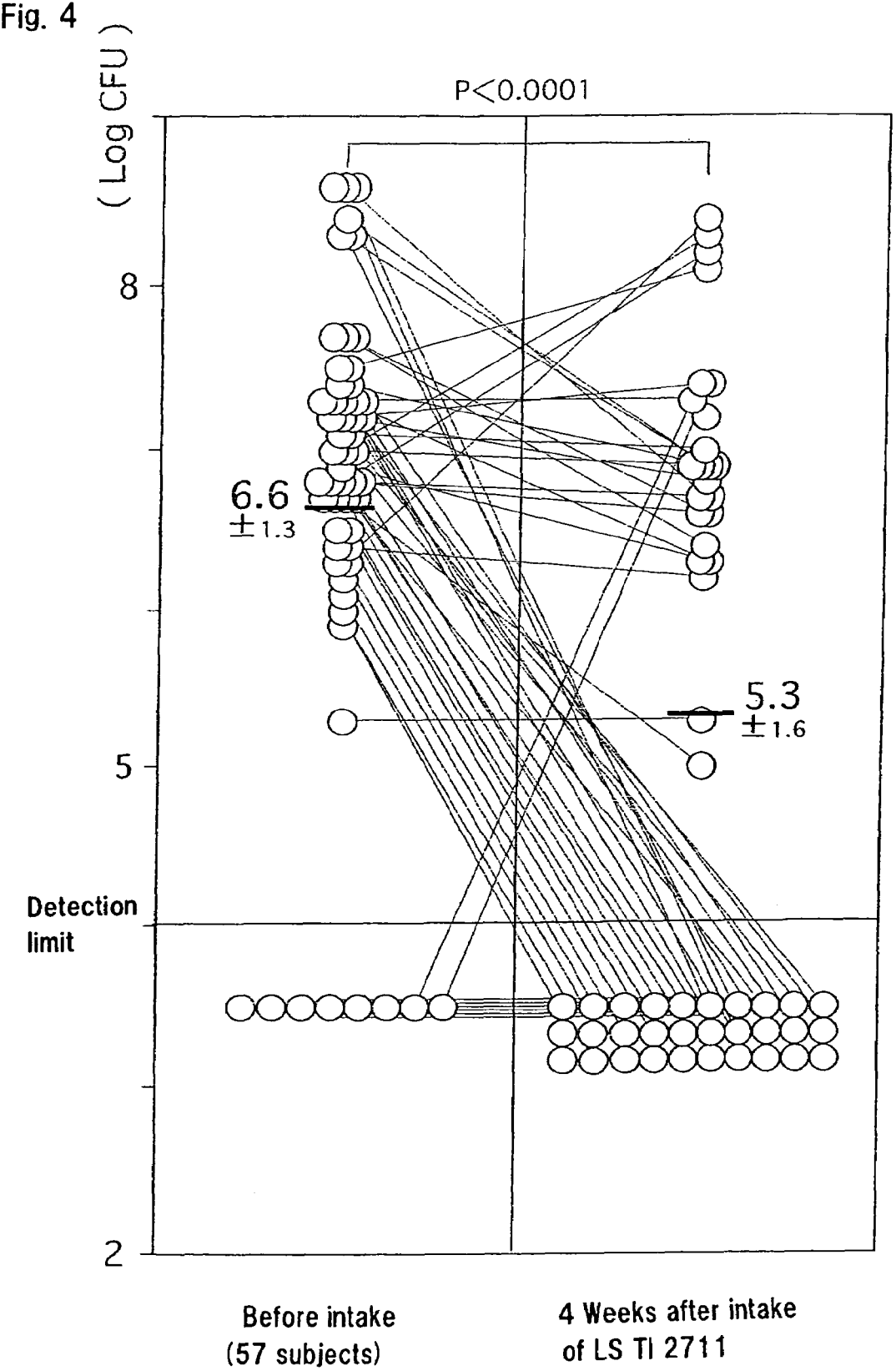
FIG. 4 is a graph showing change in the number of human intraoral periodontopathic bacteria (black-pigmented anaerobic rods, BPAR).

The obtained results for the number of intraoral periodontopathic bacteria are shown in FIG. 4. As shown in FIG. 4, before the intake, 8 persons showed a cell number below a detection limit, and the average was $10^{6.6\pm1.3}$ CFU/total saliva, whereas, after the intake of four weeks, the number of persons having a cell number below the detection limit was markedly increased to 30, and the average was $10^{5.3\pm1.6}$ CFU/total saliva (P<0.0001). Therefore, it was demonstrated that the pathogenic bacteria, i.e., periodontopathic bacteria, were eliminated and suppressed by the intake of the *Lactobacillus salivarius* TI 2711 strain.

(3) Variation in Number of Intraoral Cariogenic Bacteria (Gram-Positive mutans *Streptococci*)

Figure 5:
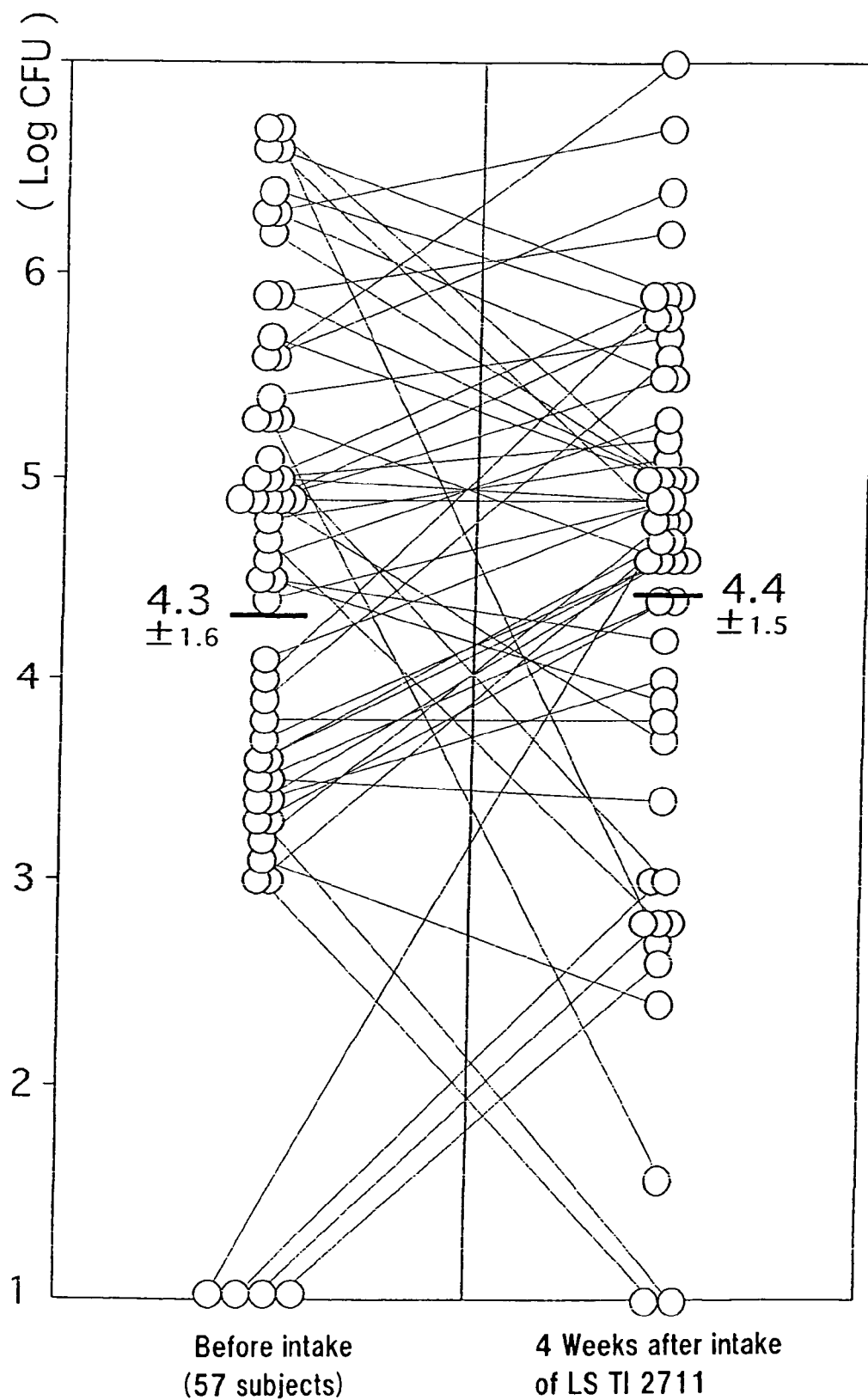
FIG. 5 is a graph showing change in the number of human intraoral mutans Streptococci.

The results obtained for the cell number of caries bacteria are shown in FIG. 5. As shown in FIG. 5, no significant difference was recognized between the cell numbers of mutans *Streptococci* in saliva before and after the intake.

(4) Variation in Number of Intraoral Lactic Acid Bacteria

Figure 6:
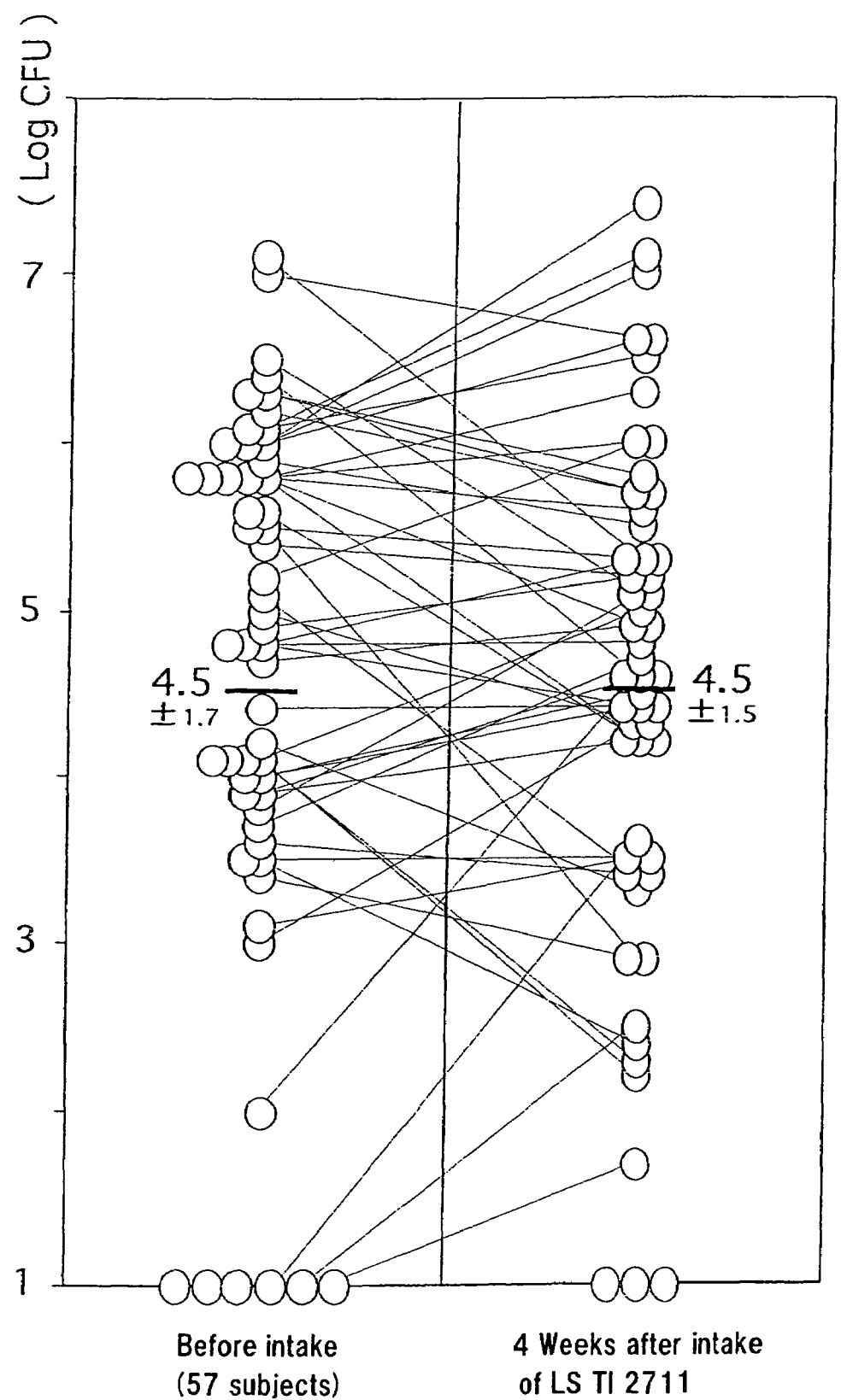
FIG. 6 is a graph showing change in the number of intraoral lactic acid bacteria.

The results obtained for the cell number of intraoral lactic acid bacteria are shown in FIG. 6. As shown in FIG. 6, no significant difference was recognized also between the cell numbers of intraoral lactic acid bacteria before and after the intake.

(5) Variation in Saliva pH

Figure 7:
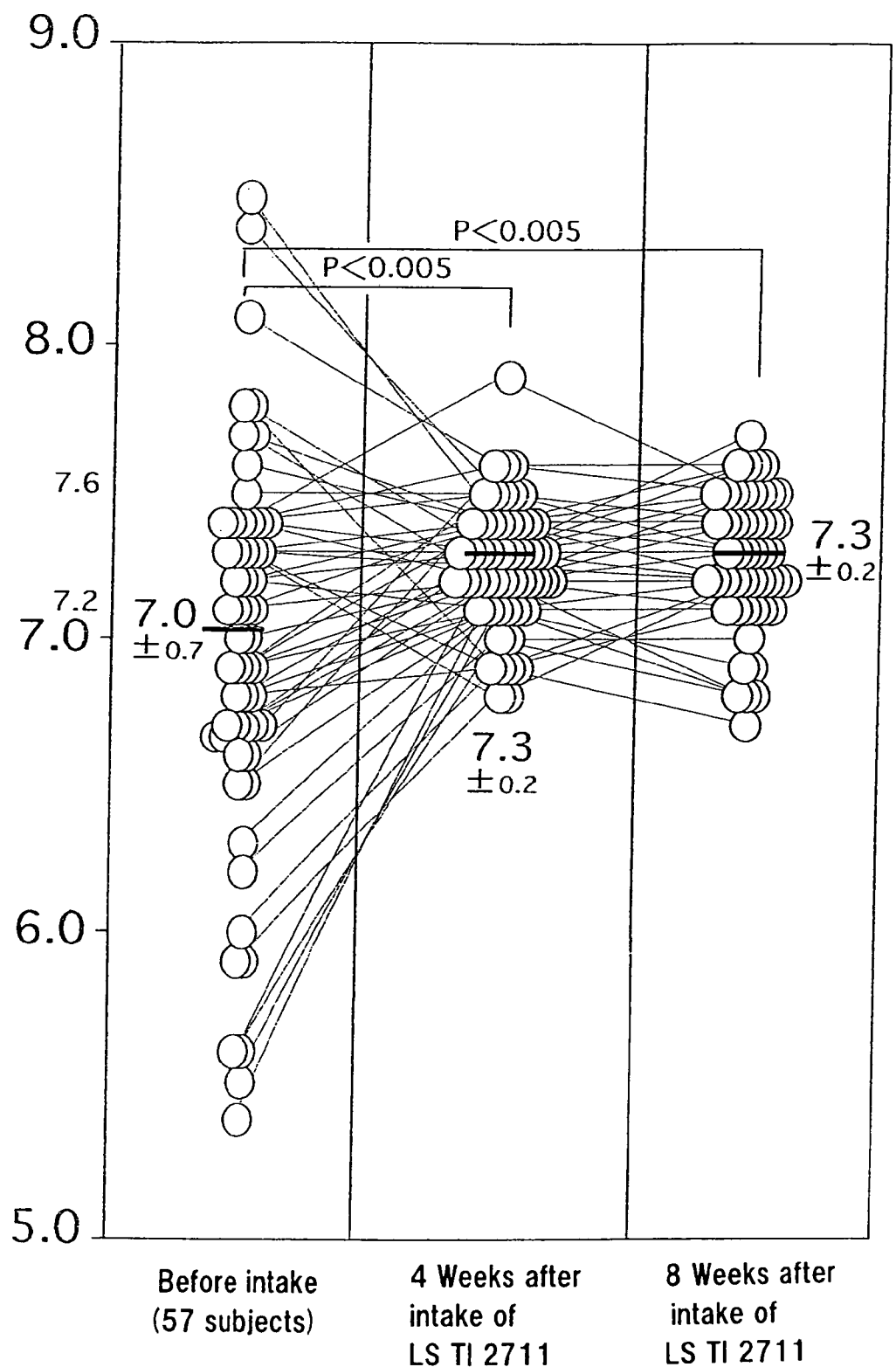
FIG. 7 is a graph showing change in pH of human saliva.

The results of the measurement of saliva pH variation are shown in FIG. 7. Before the intake, 57 persons showed a great distribution of pH (variation degree of pH), and the average was pH 7.0±0.7. However, after the intake of four weeks, the distribution of pH was reduced, and the average became pH 7.3±0.2, i.e., a value approximately the same as pH of blood, was observed. That is, it was shown that saliva pH was retained at normal level. This phenomenon was seen also after 8 weeks, pH was maintained at a normal level, and the distribution was very small. These results constitute data completely negating a doubt that, if lactic acid bacteria are administered to human, production of lactic acid should be promoted to advance caries. Thus, the results have extremely important clinical significance.

(6) Variation in Amount of Produced Insoluble Glucan in Saliva

Figure 8:
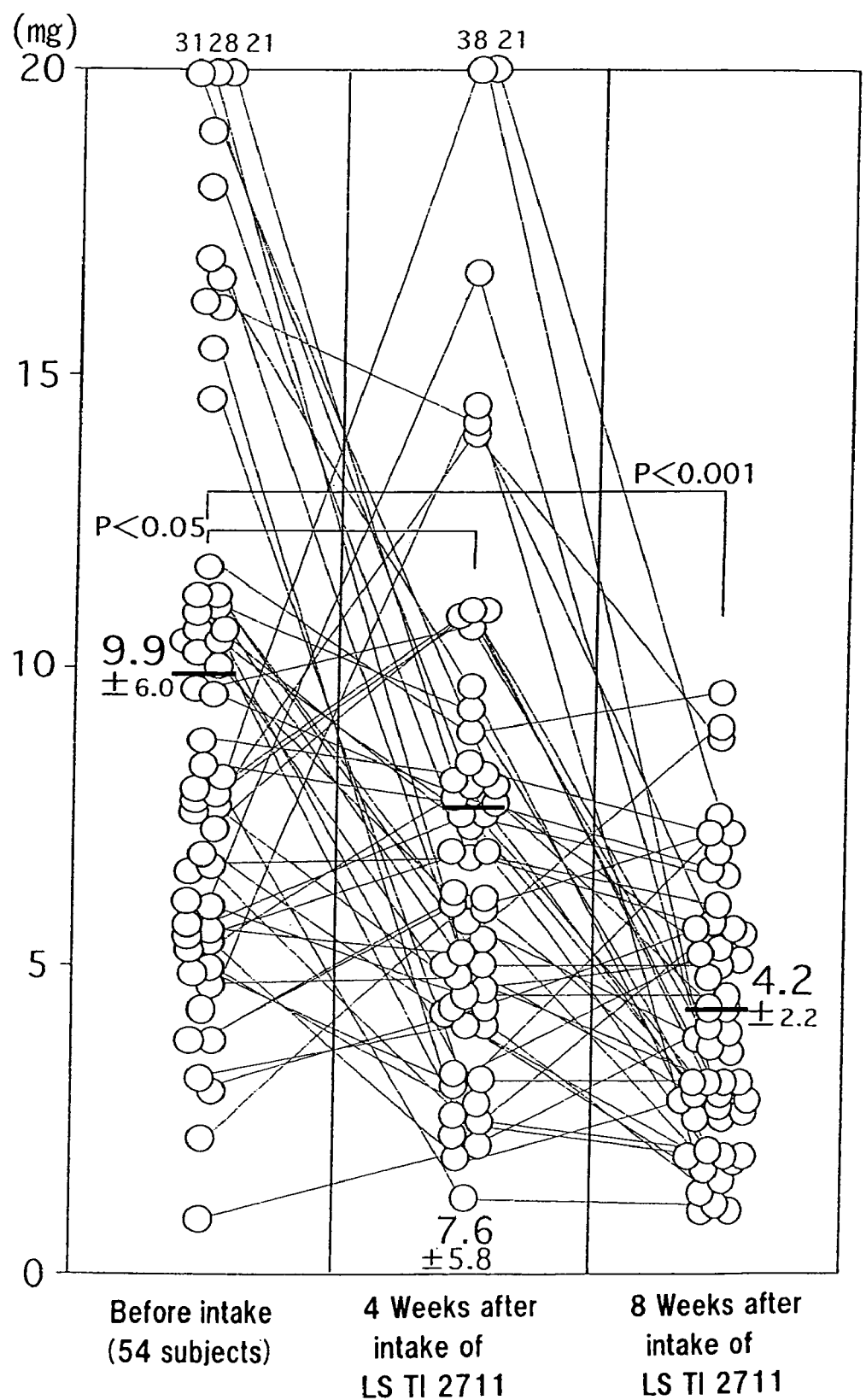
FIG. 8 is a graph showing change in the amount of insoluble glucan in human saliva.

The results of the measurement of the amount of produced insoluble glucan in saliva are shown in FIG. 8. As shown in FIG. 8, the amount of insoluble glucan in saliva before intake was 9.9±6.0 mg/total saliva in average, whereas, after the intake of four weeks, the average became 7.6±5.8 mg/total saliva (P<0.05). Thus, a statistically significant difference was recognized. Further, after eight weeks, the average became 4.2±2.2 mg/total saliva (P<0.001), and thus a dose response correlation was recognized for the intake of the *Lactobacillus salivarius* TI 2711 strain. This constitutes a part of the evidences serving as scientific grounds of effectiveness of the lactic acid bacterium strain of the present invention established by this clinical test. That is, it was found that the lactic acid bacterium strain of the present invention could prevent production of insoluble glucan, which is a major causative substance for dental plaques, and eradicate habiting places for anaerobic periodontopathic bacteria and cariogenic bacteria, and thus it could be means for suppressing development, recurrence and exacerbation of chronic infectious disease such as caries and periodontal disease. Furthermore, it was strongly suggested that intake of the *Lactobacillus salivarius* TI 2711 strain for a long period of time makes pH of saliva be at a normal level as described above and makes dental plaques hardly be formed, and thus it can suppress production of an acid in the interior of dental plaques by intraoral bacteria, and is useful for prevention of caries and periodontal disease and treatment of mild cases.

(7) Results of Measurement of Halitosis Using Halimeter

For measurement of halitosis, amounts of volatile sulfide compounds in expired air of healthy volunteers were measured by using Halimeter. One of major causes for generation of halitosis is degradation of proteins by periodontopathic bacteria. That is, since periodontopathic bacteria have markedly high activities of proteases, they easily degrade proteins in intraoral food cruds, which constitute one of nutrient sources of the bacteria, to produce halitosis causative substances, which are volatile sulfurated compounds (VSC) such as thiols and sulfides including $H_2S$ and $CH_3SH$.

Amounts of volatile sulfurated compounds in expired air of 57 healthy volunteers before the intake of confectionary tablets containing the lactic acid bacterium strain of the present invention were measured at room temperature (20° C.) using Halimeter, and follow-up measurement was performed after the intake for 20 volunteers showing an RU (Response Unit) value of 65 ppb (ppb=part per billion) or larger before the intake. The results are shown in FIG. 9.

Figure 9:
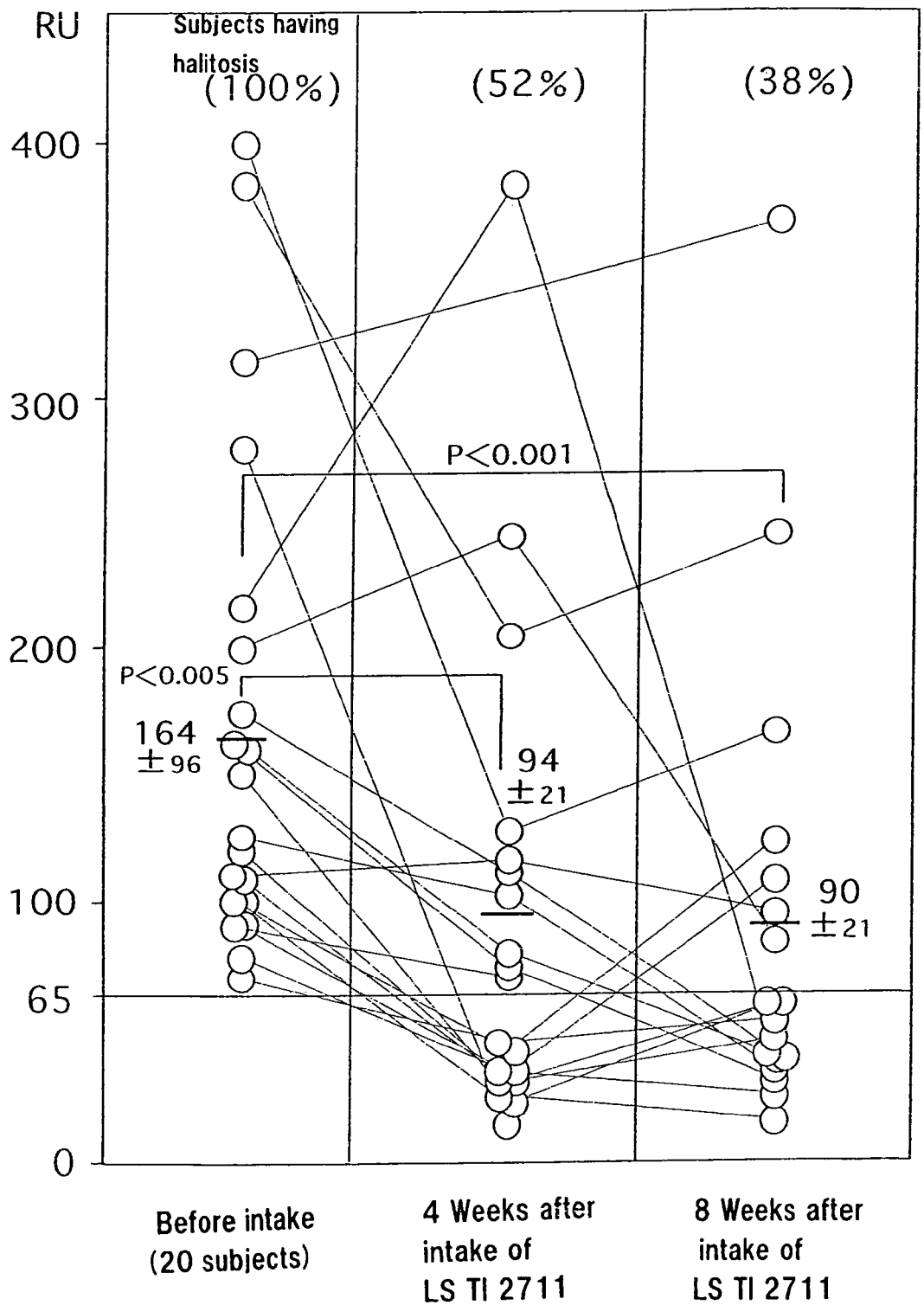
FIG. 9 is a graph showing the results of measurement of halitosis using Halimeter.

As shown in FIG. 9, the RU values for halitosis of these 20 volunteers fallen within the range of 164±96 ppb (mean±standard error) before the intake, but after the intake of four weeks, the values were reduced to 94±21 ppb, and a statistically extremely significant difference (P<0.005) was recognized.

Further, in the measurement after eight weeks, the RU values were reduced to 90±21 ppb, and there were 13 normal volunteers who gave a value of 65 ppb or smaller (P<0.001) and no halitosis.

That is, based on the number of volunteers having halitosis before the intake, which is taken as 100%, the number was decreased to 52% after four weeks, and further decreased to 38% after eight weeks.

These results substantially show a dose response correlation, indicating that halitosis can be eliminated by long term intake of the lactic acid bacterium strain of the present invention.

In addition, the fact of the suppression of periodontopathic bacteria and the fact of suppressing generation of halitosis by the lactic acid bacterium strain of the present invention, *Lactobacillus salivarius* TI 2711 strain, showed good correlation.

As a result of doctor's inquiry for the 57 volunteers, no occurrence of abdominal symptom was recognized in all cases.

TEST EXAMPLE 4

Effect of Addition of Various Oligosaccharides and Sugar Alcohols and Inoculation of *Lactobacillus salivarius* TI 2711 Strain on Suppression of Insoluble Glucan Production by *Streptococcus mutans* (in Vitro)

Test Method

5% each of xylitol, erythritol and sorbitol as sugar alcohols, and fructo-oligosaccharide and kestose as oligosaccharides were each added to a liquid medium consisting of GAM bouillon (Nissui) as a base medium and containing 0.7% glucose and 3% sucrose, and each medium was inoculated with $1\times10^7$ CFU/ml of the *Streptococcus mutans* MT 8148 strain. Then, aerobic culture was performed at 37° C. for 24 hours.

On the other hand, $1\times10^7$ CFU/ml of the *Streptococcus mutans* MT 8148 strain was inoculated to the aforementioned medium containing 5% of each sugar alcohol or oligosaccharide, and $1\times10^7$ CFU/ml of the *Lactobacillus salivarius* TI 2711 strain was further inoculated to the medium. Then, aerobic culture was similarly performed at 37° C. for 24 hours. After completion of the culture, the cell numbers of *Streptococcus mutans* MT 8148 strain and amounts of insoluble glucan were determined (according to the methods described in Test Example 1) for the both types of culture. The results are shown in Table 2.

Test Results

As shown in Table 2, among the sugar alcohols and the oligosaccharides, the substance that most strongly inhibited the production of insoluble glucan was erythritol, and erythritol alone showed about 60% inhibition. However, in the mixed culture inoculated with the *Lactobacillus salivarius* TI 2711 strain, an additive or synergistic effect of erythritol and the *Lactobacillus salivarius* TI 2711 strain was observed, i.e., 90% inhibition was observed based on the amount of insoluble glucan obtained without inoculation of the *Lactobacillus salivarius*, which was taken as 100%, and thus better results were obtained.

TABLE 2

| Oligosaccharide and sugar alcohol (5% addition) | Without inoculation of *L. salivarius* | | With inoculation of *L. salivarius* | |
|---|---|---|---|---|
| | Number of viable cells of *S. mutans* (CFU/ml) | Amount of insoluble glucan (μg/ml) | Number of viable cells of *S. mutans* (CFU/ml) | Amount of insoluble glucan (μg/ml) |
| Xylitol | $4.0 \times 10^5$ | 5,992 | $5.0 \times 10^5$ | 1,996 |
| Erythritol | $1.0 \times 10^5$ | 4,324 | $1.0 \times 10^4$ | 962 |
| Sorbitol | $4.0 \times 10^5$ | 4,384 | $3.0 \times 10^5$ | 1,691 |
| Fructo-oligosaccharide | $4.0 \times 10^5$ | 6,659 | $2.0 \times 10^5$ | 1,892 |
| Kestose | $5.0 \times 10^5$ | 7,392 | $2.0 \times 10^5$ | 2,886 |
| Control (base medium) | $4.0 \times 10^5$ | 11,160 | $2.0 \times 10^5$ | 2,394 |

EXAMPLE 1

Preparation of Dry Cells of *Lactobacillus salivarius* TI 2711 Strain

The *Lactobacillus salivarius* TI 2711 strain was inoculated into Briggs liver broth containing 0.3% calcium carbonate and cultured at 37° C. for 18 hours as static culture. After completion of the culture, the culture was centrifuged at 7,000 rpm for 15 minutes to obtain concentrated cells in a 1/100 volume.

Then, a dispersing medium containing 5% (by weight) of sodium glutamate, 5% (by weight) of soluble starch and 5% (by weight) of sucrose was mixed with the concentrated cells in the same amounts, and the mixture was adjusted to pH 7.0, frozen at a temperature of −40° C. or lower and lyophilized. The resulting lyophilized cells were made into powder on a 60 mesh sieve to obtain a lactic acid bacterium powder of the present invention. As for storage stability of the bacterium of the present invention, even when the lactic acid bacterium powder was stored at room temperature (24° C.) for 10 months under a sealed condition (aluminum laminated bag), no reduction in the cell number was recognized.

EXAMPLE 2

Preparation of Pharmaceutical Live Bacterium Preparation (Tablet)

According to the provisions of the 12th revised Japanese Pharmacopoeia Guidebook, General Rules for Pharmaceutical Preparation, "Tablet", 2 g of the dry cell powder of the *Lactobacillus salivarius* TI 2711 strain (cell number: equivalent to $5\times10^9$ CFU/g) prepared in Example 1, 161 g of lactose (Japanese Pharmacopoeia), 116 g of starch (Japanese Pharmacopoeia), 20 g of binder polyvinylpyrrolidone K25 (Japanese Pharmacopoeia) and 0.8 g of magnesium stearate (Japanese Pharmacopoeia) as a lubricant were added and uniformly mixed, and the mixture was molded by compression molding by using a tablet making machine to obtain 290 g of plain tablets (300 mg per tablet).

EXAMPLE 3

Preparation of Food Containing Lactic Acid Bacterium (Confectionary Tablet)

By referring to the 12th revised Japanese Pharmacopoeia Guidebook, General Rules for Pharmaceutical Preparation, "Tablet", 0.7 g of the dry cell powder of the *Lactobacillus salivarius* TI 2711 strain (cell number: equivalent to $5\times10^9$ CFU/g), 47 g of erythritol, 47 g of sorbitol, 2.5 g of l-menthol, 1.5 g of a flavor (lime) and 1.3 g of sucrose fatty acid ester, which is designated as a food additive in Japan, as a lubricant were added, uniformly mixed, and the mixture was molded by compression molding by using a tablet making machine to obtain 95 g of plain tablets (300 mg per tablet).

EXAMPLE 4

Preparation of Food Containing Lactic Acid Bacterium (Chewing Gum)

In an amount of 10 g of the dry cell powder of the *Lactobacillus salivarius* TI 2711 strain (cell number: equivalent to $5\times10^9$ CFU/g), 160 g of erythritol, 160 g of sorbitol, 20 g of peppermint oil as a flavor and 150 g of gum base (food additive) were weighed beforehand. The gum base was sufficiently kneaded by using a kneader for production of chewing gum, added portionwise with a preliminarily prepared uniform mixture of erythritol and sorbitol as sweeteners and the dry cell powder of the *Lactobacillus salivarius* TI 2711 strain during the kneading of the gum base, uniformly kneaded, finally added with peppermint oil for giving flavor, and uniformly kneaded. After completion of the kneading, a mass of chewing gum was removed from the kneader and subjected to rolling using rollers to prepare a chewing gum plate having a thickness of 3 mm. The chewing gum plate was aged in a thermostatic chamber for 2 days and cut into a size of marketed plate chewing gum to prepare chewing gum.

EXAMPLE 5

Preparation of Food Containing Lactic Acid Bacterium (Fermented Milk)

Preparation by Mixed Culture Using Starter Bacterium, *Lactobacillus acidophilus*, and *Lactobacillus salivarius* TI 2711 Strain A starter bacterium for fermented milk, *Lactobacillus acidophilus*, was inoculated to a reduced defatted medium containing 23 g of skimmed milk, 1.0 g of yeast extract and 0.06 g of ascorbic acid and cultured at 37° C. for 16 hours as static culture to obtain a bulk starter.

The culture broth of *Lactobacillus salivarius* TI 2711 strain obtained in Example 1 and the bulk starter culture broth prepared above were inoculated in an amount of 5% each to a raw material mixture containing fresh milk and skimmed milk, and culture was performed at 37° C. for 16 hours to obtain fermented milk. The fermented milk prepared by using the strain of the present invention showed good flavor and good taste, and was a highly acceptable product.

INDUSTRIAL APPLICABILITY

As a result of the in vitro test, in vivo test using germfree mice and long term clinical test (n=57) performed for the *Lactobacillus salivarius* TI 2711 strain of the present invention, effectiveness of the strain on normalization of intraoral microflora, suppression of periodontopathic bacteria and cariogenic bacteria and prevention of generation of halitosis was verified in all of the tests.

That is, by taking or ingesting the strain of the present invention, intraoral microflora can be normalized, as a result, periodontopathic bacteria and cariogenic bacteria can be suppressed, and thus generation of halitosis can be suppressed. Therefore, the strain of the present invention is useful as an ingredient for a live bacterium preparation or food containing a lactic acid bacterium that can be used for maintaining pH of saliva at a physiologically normal level, prevention and treatment of gingivitis, periodontitis and periodontal disease, prevention and treatment of dental caries, prevention of generation of halitosis and elimination of halitosis.

I claim:

1. A live bacterium preparation or food for treatment of gingivitis, periodontitis or periodontal disease, which comprises live cells of a lactic acid bacterium, *Lactobacillus salivarius* TI 2711 strain (FERM BP-7974) as an active ingredient.

2. A live bacterium preparation or food for treatment of dental caries, which comprises live cells of a lactic acid bacterium, *Lactobacillus salivarius* TI 2711 strain (FERM BP-7974), as an active ingredient.

3. A live bacterium preparation or food for treatment of halitosis, which comprises live cells of a lactic acid bacterium, *Lactobacillus salivarius* TI 2711 strain (FERM BP-7974), as an active ingredient.

4. A live cell obtained by pure culture of a lactic acid bacterium, *Lactobacillus salivarius* TI 2711 strain (FERM BP-7974).

5. A dry live cell obtained by pure culture of a lactic acid bacterium, *Lactobacillus salivarius* TI 2711 strain (FERM BP-7974).

6. A composition comprising a live lactic acid bacterium, *Lactobacillus salivarius* TI 2711 strain (FERM BP-7974), and an oral care drug.

7. The composition according to claim 6, wherein the oral care drug is selected from the group consisting of sugar alcohols and oligosaccharides.

8. The composition according to claim 7, wherein the oral care drug is erythritol.

9. An isolated strain of *Lactobacillus salivarius* TI 2711 strain (FERM BP-7974).

10. The live bacterium preparation or food according to claim 2, wherein the *Lactobacillus salivarius* TI 2711 strain has an ability that, when the strain is cultured with *Streptococcus mutans* at 37° C. for 24 hours, it can reduce amount of insoluble glucan produced by *Streptococcus mutans* to a level of 20% or lower compared with amount of insoluble glucan produced by *Streptococcus mutans* cultured alone.

11. The live bacterium preparation or food according to claim 1, wherein the *Lactobacillus salivarius* TI 2711 strain has an ability that, when oral cavity of a mouse is infected with a periodontopathic bacterium, *Porphyromonas gingivalis*, by administration of the bacterium to the oral cavity once a day for consecutive three days in an amount of $1 \times 10^9$ CFU each, and then the *Lactobacillus salivarius* TI 2711 strain is administered to the oral cavity of the mouse once a day for consecutive three days in an amount of $1 \times 10^9$ CFU each, the *Lactobacillus salivarius* TI 2711 strain can reduce cell count of the periodontopathic bacterium with significance of $P<0.001$ according to the Wilcoxon test.

12. The live bacterium preparation or food according to claim 2, wherein the *Lactobacillus salivarius* TI 2711 strain has an ability that, when oral cavity of a mouse is infected with a cariogenic bacterium, *Streptococcus mutans*, by administration of the bacterium to the oral cavity once a day for consecutive three days in an amount of $1 \times 10^9$ CFU each, and then the *Lactobacillus salivarius* TI 2711 strain is administered to the oral cavity of the mouse once a day for consecutive three days in an amount of $1 \times 10^9$ CFU each, the *Lactobacillus salivarius* TI 2711 strain can reduce cell count of the cariogenic bacterium with significance of $P<0.01$ according to the Wilcoxon test.

13. The composition according to claim 6, which shows higher effect for suppression of *Streptococcus mutans* proliferation and insoluble glucan production by *Streptococcus mutans* compared with sum of the effect obtainable by use of the lactic acid bacterium alone and the effect obtainable by use of an oral care drug alone, and
wherein the oral care drug is erythritol.

14. A composition comprising the isolated strain of *Lactobacillus salivarius* TI 2711 strain (FERM BP-7974) according to claim 9.

15. The isolated strain of *Lactobacillus salivarius* TI 2711 strain (FERM BP-7974) according to claim 9, wherein the *Lactobacillus salivarius* TI 2711 strain has an ability that when the strain is cultured with *Streptococcus mutans* at 37° C. for 24 hours, the strain can reduce the amount of insoluble glucan produced by *Streptococcus mutans* as compared with amount of insoluble glucan produced by *Streptococcus mutans* cultured alone.

* * * * *